United States Patent
Shimizukawa

(10) Patent No.: US 8,618,491 B2
(45) Date of Patent: Dec. 31, 2013

(54) RADIOGRAPHIC IMAGE IMAGING DEVICE, RADIOGRAPHIC IMAGE IMAGING METHOD AND STORAGE MEDIUM STORING RADIOGRAPHIC IMAGE IMAGING PROGRAM

(75) Inventor: Sho Shimizukawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 24 days.

(21) Appl. No.: 13/116,685

(22) Filed: May 26, 2011

(65) Prior Publication Data
US 2012/0076274 A1    Mar. 29, 2012

(30) Foreign Application Priority Data
Sep. 28, 2010 (JP) .................. 2010-217330

(51) Int. Cl.
*G01T 1/175* (2006.01)
(52) U.S. Cl.
USPC .................................................. 250/370.09
(58) Field of Classification Search
USPC .................................................. 250/370.09
See application file for complete search history.

(56) References Cited

U.S. PATENT DOCUMENTS

| | | | | |
|---|---|---|---|---|
| 5,541,656 A | * | 7/1996 | Kare et al. | 348/333.02 |
| 7,486,333 B2 | * | 2/2009 | Kawakami | 348/372 |
| 2002/0034964 A1 | * | 3/2002 | Bannai et al. | 455/556 |
| 2002/0037711 A1 | * | 3/2002 | Mizutani | 455/414 |
| 2006/0006842 A1 | * | 1/2006 | Miskovic et al. | 320/128 |
| 2008/0312852 A1 | * | 12/2008 | Maack | 702/63 |
| 2009/0189761 A1 | * | 7/2009 | Nishino et al. | 340/540 |
| 2009/0207973 A1 | * | 8/2009 | Yi | 378/101 |
| 2009/0251416 A1 | * | 10/2009 | Fujii et al. | 345/168 |
| 2010/0171751 A1 | * | 7/2010 | Kim | 250/370.04 |
| 2010/0230606 A1 | * | 9/2010 | Liu et al. | 250/370.04 |

FOREIGN PATENT DOCUMENTS

| | | |
|---|---|---|
| JP | 2005-006888 A | 1/2005 |
| JP | 2006-043191 A | 2/2006 |
| JP | 2006-95020 A | 4/2006 |
| JP | 2009-032854 A | 2/2009 |

* cited by examiner

*Primary Examiner* — Marcus Taningco
(74) *Attorney, Agent, or Firm* — Sughrue Mion, PLLC

(57) ABSTRACT

A radiographic image imaging device is provided. The device includes: an acquisition component that acquires battery remaining power amount information representing an amount of power remaining in a battery, which is incorporated in a portable radiographic image imaging device and supplies power to the portable radiographic image imaging device, the portable radiographic image imaging device detecting radiation irradiated at a subject of imaging and generating a radiographic image; a calculation component that calculates a possible standby duration of the portable radiographic image imaging device on the basis of the battery remaining power amount information acquired by the acquisition component and a number of images of the portable radiographic image imaging device; and a display component that displays the number of images and the possible standby duration.

18 Claims, 10 Drawing Sheets

FIG.4
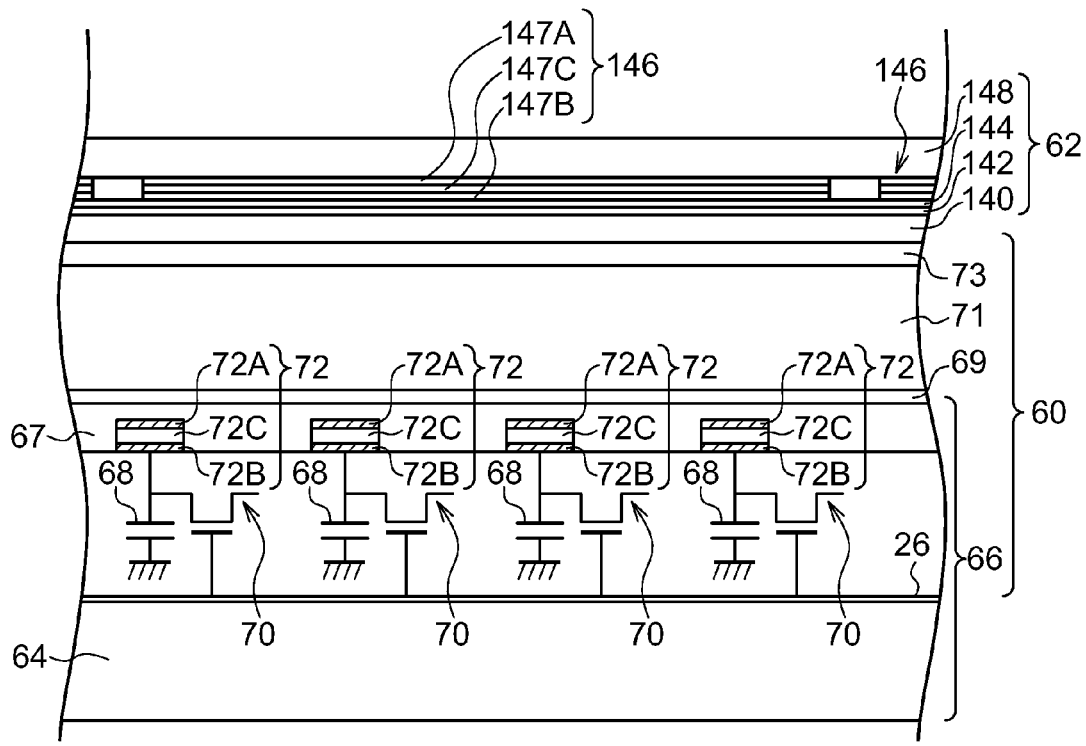
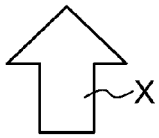
FIG.5
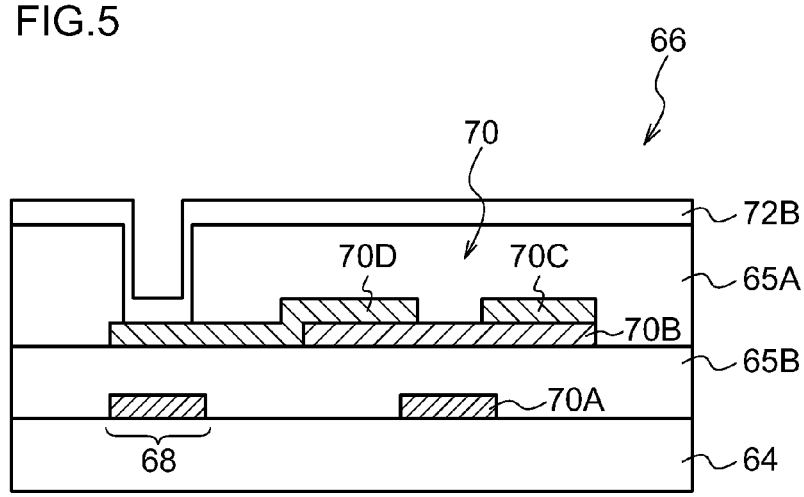

RADIOGRAPHIC IMAGE IMAGING DEVICE, RADIOGRAPHIC IMAGE IMAGING METHOD AND STORAGE MEDIUM STORING RADIOGRAPHIC IMAGE IMAGING PROGRAM

CROSS-REFERENCE TO RELATED APPLICATION

This application claims priority under 35 USC 119 from Japanese Patent Application No. 2010-217330 filed on Sep. 28, 2010, the disclosure of which is incorporated by reference herein.

BACKGROUND OF THE INVENTION

1. Field of the Invention

The present invention relates to a radiographic image imaging device, a radiographic image imaging method and a storage medium storing a radiographic image imaging program, and particularly relates to a radiographic image imaging device, radiographic image imaging method and a storage medium storing radiographic image imaging program that image radiographic images represented by radiation that has been emitted from a radiation source and passed through a subject of examination.

2. Description of the Related Art

In recent years, radiographic detectors such as flat panel detectors (FPDs) in which radiation-sensitive layers are disposed on thin film transistor (TFT) active matrix substrates, and that detect irradiated radiation such as X-rays or the like and output electronic signals representing radiographic images represented by the detected radiation, have become practical. These radiographic detectors have advantages over related art imaging plates in that images can be checked immediately and video images can be checked.

Portable radiographic imaging devices (hereinafter also referred to as electronic cassettes) that incorporate these radiation detectors and memorize radiographic image data outputted from the radiation detectors have also become practical. These electronic cassettes have excellent portability, so may image patients who have simply been placed on stretchers, beds and the like. Moreover, adjustment of imaging locations is easy, by changing positions of the electronic cassettes. Therefore, even imaging of patients who cannot move may be administered with flexibility.

Electronic cassettes are commonly driven by batteries. Remaining charge amounts in the batteries need to be properly managed.

Therefore, in Japanese Patent Application Laid-Open (JP-A) No. 2006-95020, a technology is disclosed that calculates a possible number of images for a radiation detector on the basis of a charged amount of a battery and displays the number of possible images at a display. Specifically, a technology is disclosed in which an expected number of images is registered in advance in a mode such as an imaging menu, and a result of comparison between the calculated number of possible images and the expected number of images is displayed at the display.

JP-A No. 2005-6888 has disclosed a technology that calculates a number of possible images for an X-ray detector on the basis of the remaining capacity of a battery, and carries out appropriate processing in accordance with the number of possible images.

JP-A No. 2006-43191 has disclosed a technology that, on the basis of a maximum number of images per individual subject to be imaged (per patient) when an imaging device is used in a hospital or the like, determines a fixed limit relating to remaining charge amounts that represents a replacement period of a battery.

The electrical power that is consumed by an electronic cassette is not just the power that is consumed by imaging but also includes power that is consumed during standby, when imaging is not being performed. Moreover, if, for example, imaging is carried out a plural number of times for different locations of a single patient with different postures and the like, then standby durations between images and durations that vary with, for example, posture differ between patients. Therefore, the power that is consumed in a single examination differs between patients.

However, in the related art technologies described above, no account is taken of the power that is consumed during standby. Therefore, what amount of time standby is possible for is not known, and there is a risk that a battery may run short of charge in the middle of an examination.

SUMMARY OF THE INVENTION

The present invention has been made to solve the problem described above, and an object of the present invention is to provide a radiographic image imaging device, a radiographic image imaging method and a radiographic image imaging program that may avoid a battery of a portable radiographic image imaging device running short during an examination.

A radiographic image imaging device relating to an aspect of the present invention includes: an acquisition component that acquires battery remaining power amount information representing an amount of power remaining in a battery, which is incorporated in a portable radiographic image imaging device and supplies power to the portable radiographic image imaging device, the portable radiographic image imaging device detecting radiation irradiated at a subject of imaging and generating a radiographic image; a calculation component that calculates a possible standby duration of the portable radiographic image imaging device on the basis of the battery remaining power amount information acquired by the acquisition component and a number of images of the portable radiographic image imaging device; and a display component that displays the number of images and the possible standby duration.

According to this invention, a possible standby duration of the portable radiographic image imaging device is calculated and displayed on the basis of a remaining amount of power in the battery that supplies power to the portable radiographic image imaging device and a number of images to be imaged by the portable radiographic image imaging device. Thus, particularly when plural images are to be imaged, how much of a margin for standby durations between images there is may be ascertained, and the battery of the portable radiographic image imaging device may be prevented from running short in the middle of an examination.

A radiographic image imaging method relating to another aspect of the present invention includes: acquiring battery remaining power amount information representing an amount of power remaining in a battery, which is incorporated in a portable radiographic image imaging device and supplies power to the portable radiographic image imaging device, the portable radiographic image imaging device detecting radiation irradiated at a subject of imaging and generating a radiographic image; calculating a possible standby duration of the portable radiographic image imaging device on the basis of the acquired battery remaining power amount information and a number of images of the portable radiographic image imaging device; and displaying the number of images and the possible standby duration.

According to this invention, a possible standby duration of the portable radiographic image imaging device is calculated and displayed on the basis of a remaining amount of power in the battery that supplies power to the portable radiographic image imaging device and a number of images of the portable radiographic image imaging device. Thus, particularly when plural images are to be imaged, how much of a margin for standby durations between images there is may be ascertained, and the battery of the portable radiographic image imaging device may be prevented from running short in the middle of an examination.

A storage medium readable by a computer, the storage medium storing a program of instructions executable by the computer to function as a radiographic image imaging device that includes: an acquisition component that acquires battery remaining power amount information representing an amount of power remaining in a battery, which is incorporated in a portable radiographic image imaging device and supplies power to the portable radiographic image imaging device, the portable radiographic image imaging device detecting radiation irradiated at a subject of imaging and generating a radiographic image; a calculation component that calculates a possible standby duration of the portable radiographic image imaging device on the basis of the battery remaining power amount information acquired by the acquisition component and a number of images of the portable radiographic image imaging device; and a display component that displays the number of images and the possible standby duration.

According to this invention, a possible standby duration of the portable radiographic image imaging device is calculated and displayed on the basis of a remaining amount of power in the battery that supplies power to the portable radiographic image imaging device and a number of images of the portable radiographic image imaging device. Thus, particularly when plural images are to be imaged, how much of a margin for standby durations between images there is may be ascertained, and the battery of the portable radiographic image imaging device may be prevented from running short in the middle of an examination.

According to the present invention, there is an effect in that the battery of the portable radiographic image imaging device may be prevented from running short in the middle of an examination.

BRIEF DESCRIPTION OF THE DRAWINGS

FIG. 4 is a sectional diagram schematically illustrating a radiation detector and a radiation detection section relating to the exemplary embodiment.

FIG. 5 is a sectional diagram illustrating structure of a thin film transistor and capacitor of the radiation detector relating to the exemplary embodiment.

DETAILED DESCRIPTION OF THE INVENTION

Figure 1:
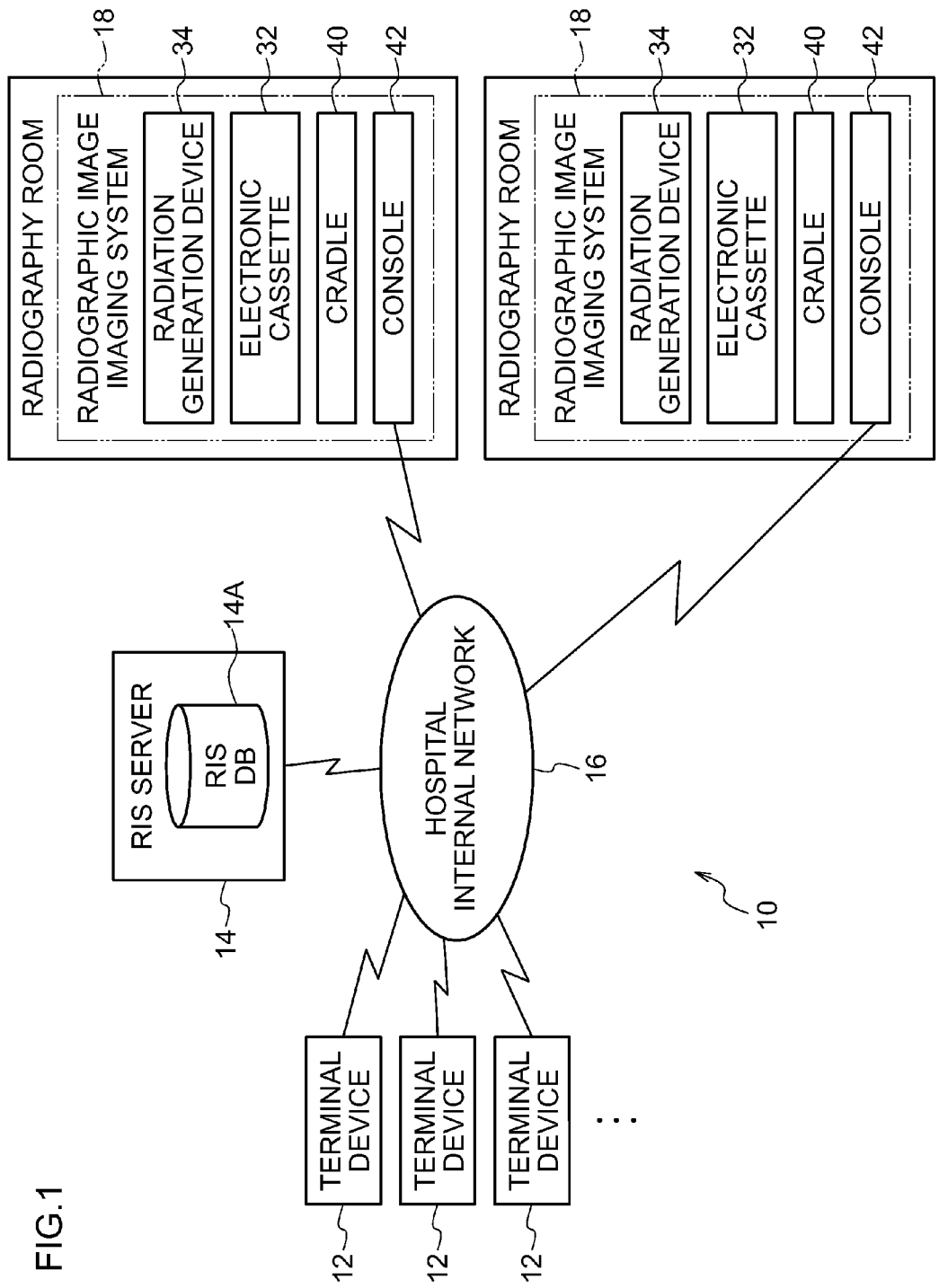
FIG. 1 is a block diagram illustrating structure of a radiology information system relating to an exemplary embodiment.

Herebelow, a mode for carrying out the present invention is described in detail with reference to the attached drawings. Herein, an example is described in which the present invention is applied to a radiographic image imaging system that performs imaging of radiographic images using a portable radiographic imaging device (hereinafter referred to as an electronic cassette).

First, a configuration of a radiology imaging system (hereinafter referred to as an RIS) 10 relating to the present exemplary embodiment is described.

The RIS 10 is a system for administering information of clinical appointments, medical records and so forth in a radiology department, and constitutes a portion of a hospital information system (hereinafter referred to as an HIS).

The RIS 10 is constituted with a plural number of imaging request terminal devices (hereinafter referred to as terminal devices) 12, an RIS server 14 and a radiographic image imaging system (hereinafter referred to as an imaging system) 18 being connected to a hospital internal network 16, which is formed with a wired or wireless LAN (local area network) or the like. The imaging system 18 is disposed in individual radiography imaging rooms (or operating rooms) in the hospital. Herein, the RIS 10 constitutes a portion of the HIS provided in the same hospital, and an HIS server (not illustrated) that administers the HIS as a whole is also connected to the hospital internal network 16.

Each terminal device 12 is for a doctor, a radiographer or the like to input and monitor clinical information, facility reservations and the like. Imaging requests for radiographic images, imaging bookings and the like are also conducted through the terminal device 12. The terminal device 12 is constituted to include a personal computer with a display device, and is connected with the RIS server 14 via the hospital internal network 16, enabling communications therebetween.

The RIS server 14 receives imaging requests from the terminal devices 12 and manages an imaging schedule for radiographic images at the imaging system 18. The RIS server 14 is constituted to include a database 14A.

The database 14A is constituted to include: information relating to patients, such as information on attributes (name, gender, date of birth, age, blood type, body weight, a patient identification (ID) number and so forth) of each patient (subject of examination), medical history, treatment history, previously imaged radiographic images, and the like; information relating to electronic cassettes 32 of the imaging system 18, such as an identification number (ID information) of each electronic cassette 32 and the type, size, sensitivity, applicable locations of imaging (details of imaging requests that can be handled), the date of first use, the number of uses, and the like; and environmental information representing environments in which the electronic cassettes 32 are used to image radiographic images, which is to say environments in which the electronic cassettes 32 are employed (for example, a radiographic imaging room, an operating room and the like).

The imaging system 18 carries out imaging of radiographic images in response to instructions from the RIS server 14, in accordance with control by doctors, radiographers and the like. The imaging system 18 is provided with a radiation generation device 34, the electronic cassette 32, a cradle 40, and a console 42. The radiation generation device 34 irradiates radiation X, constituted with radiation amounts depending on exposure conditions, from a radiation source 130 (see FIG. 2) at a subject of examination. The electronic cassette 32 incorporates a radiation detector 60 (see FIG. 3) that absorbs radiation X that has passed through an imaging location of the subject of examination and generates electronic charges. The cradle 40 charges a battery incorporated in the electronic cassette 32. The console 42 controls the electronic cassette 32, the radiation generation device 34 and the cradle 40.

The console 42 acquires various kinds of information contained in the database 14A from the RIS server 14, memorizes the information in an HDD 110 (see FIG. 10, which is described below, and controls the electronic cassette 32, the radiation generation device 34 and the cradle 40 in accordance with this information.

Figure 2:
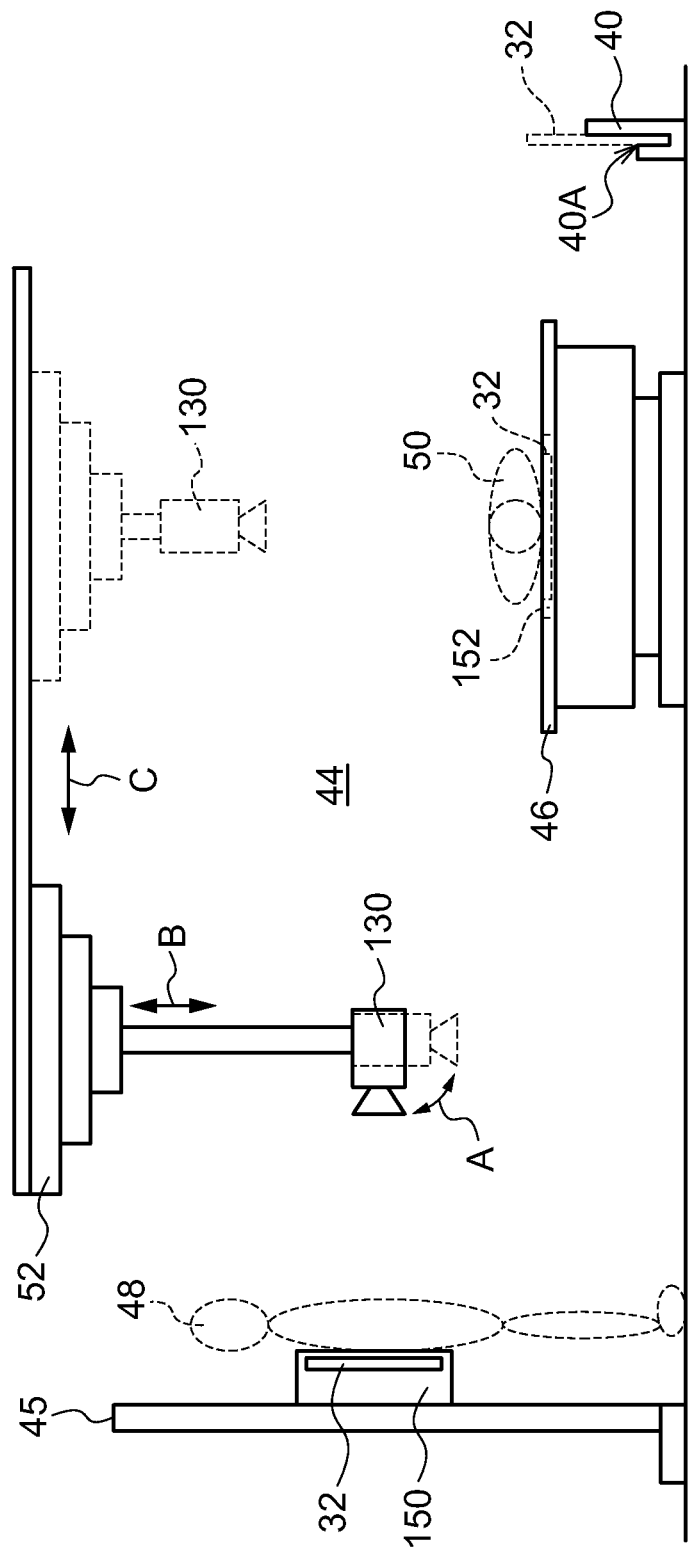
FIG. 2 is a side elevation illustrating an example of a state of arrangement of devices in a radiographic imaging room of a radiographic image imaging system relating to the exemplary embodiment.

FIG. 2 illustrates an example of a state of arrangement of devices in a radiography imaging room 44 of the imaging system 18 relating to the present exemplary embodiment.

As illustrated in FIG. 2, in the radiography imaging room 44, a standing rack 45 that is used when radiographic imaging is being carried out on an examinee in a standing position and a reclining rack 46 that is used when radiographic imaging is being carried out on an examinee in a reclining position are provided. A space forward of the standing rack 45 serves as an imaging position 48 of the examinee when radiographic imaging is being carried out in the standing position, and a space upward of the reclining rack 46 serves as an imaging position 50 of the examinee when radiographic imaging is being carried out in the reclining position.

A retention portion 150 that retains the electronic cassette 32 is provided at the standing rack 45. When a radiographic image is being imaged in the standing position, the electronic cassette 32 is retained by the retention portion 150. Similarly, a retention portion 152 that retains the electronic cassette 32 is provided at the reclining rack 46. When a radiographic image is being imaged in the reclining position, the electronic cassette 32 is retained by the retention portion 152.

In the radiography imaging room 44, in order that both radiographic imaging in the standing position and radiographic imaging in the reclining position are possible with radiation from the single radiation source 130, a support and movement mechanism 52 is provided that supports the radiation source 130 to be turnable (in the direction of arrow A in FIG. 2) about a horizontal axis, movable in a vertical direction (the direction of arrow B in FIG. 2) and movable in a horizontal direction (the direction of arrow C in FIG. 2). The support and movement mechanism 52 is provided with each of a drive source that turns the radiation source 130 about the horizontal axis, a drive source that moves the radiation source 130 in the vertical direction and a drive source that moves the radiation source 130 in the horizontal direction.

In the cradle 40, an accommodation portion 40A capable of accommodating the electronic cassette 32 is formed.

When the electronic cassette 32 is accommodated in the accommodation portion 40A of the cradle 40, the battery incorporated in the electronic cassette 32 is charged up. When a radiographic image is to be imaged, the electronic cassette 32 is taken from the cradle 40 by a radiographer or the like. If a posture for imaging is to be the standing position, the electronic cassette 32 is retained at the retention portion 150, and if the posture for imaging is to be the reclining position, the electronic cassette 32 is retained at the retention portion 152.

In the imaging system 18 relating to the present exemplary embodiment, the radiation generation device 34 and the console 42 are connected by respective cables, and various kinds of information are exchanged by communications by wire. The cables connecting the radiation generation device 34 and the console 42 are not illustrated in FIG. 2. Various kinds of information are also exchanged between the electronic cassette 32 and the console 42 by wireless communications. Note that communications between the radiation generation device 34 and the console 42 may be implemented by wireless communications.

The electronic cassette 32 is not used only in conditions in which it is retained by the retention portion 150 of the standing rack 45 or the retention portion 152 of the reclining rack 46. The electronic cassette 32 is portable, and therefore may be used in conditions in which it is not retained at a retention portion.

Figure 3:
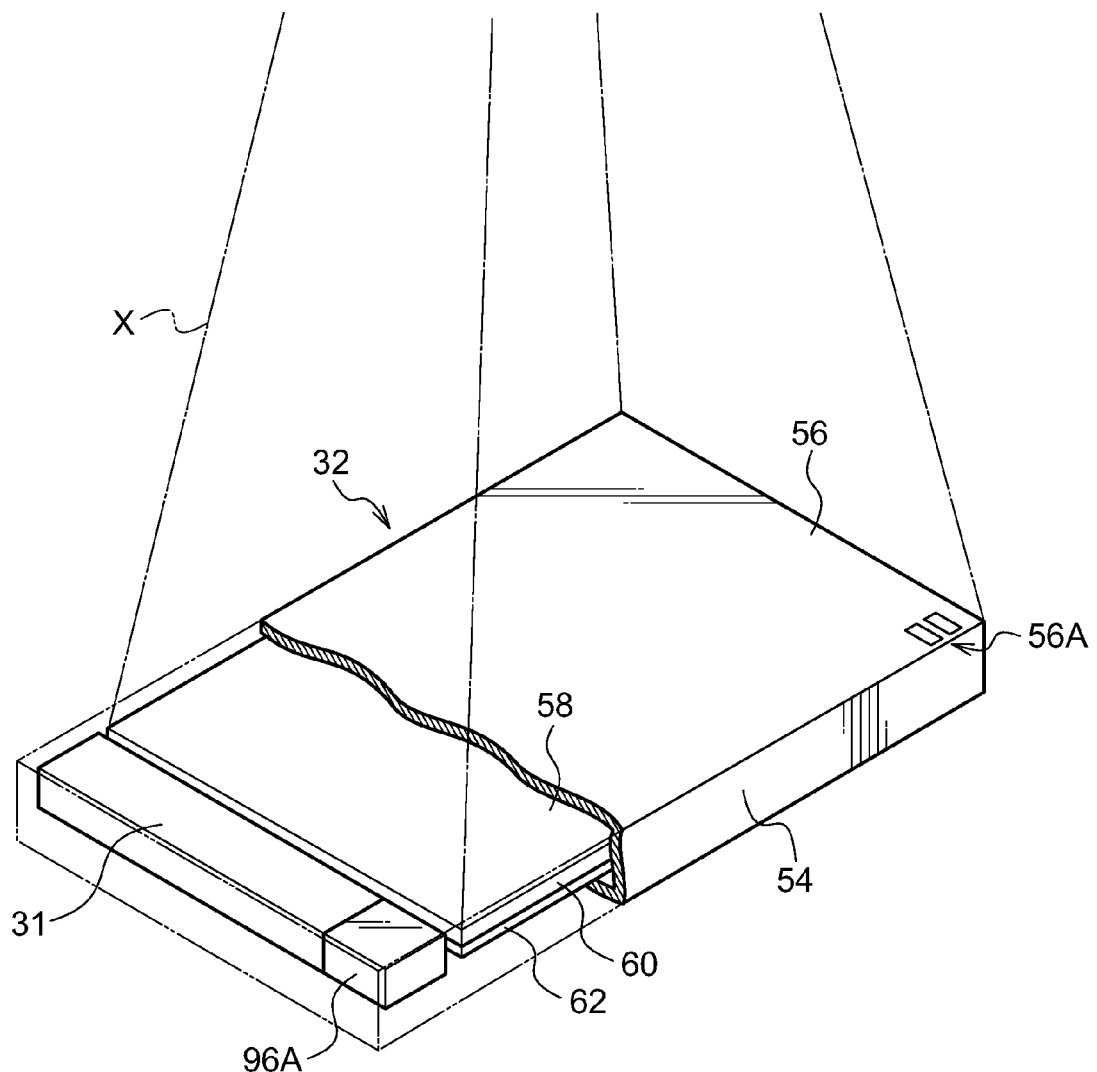
FIG. 3 is a cutaway perspective diagram illustrating an internal configuration of an electronic cassette relating to the exemplary embodiment.

FIG. 3 illustrates internal structure of the electronic cassette 32 relating to the present exemplary embodiment.

As illustrated in FIG. 3, the electronic cassette 32 is provided with a housing 54 formed of a material that transmits the radiation X, and the electronic cassette 32 is structured to be waterproof and tightly sealed. During use in an operating room or the like, blood and saprophytic bacteria and the like may adhere to the electronic cassette 32. Therefore, the electronic cassette 32 is structured to be waterproof and tightly sealed, and is washed with disinfectant as required. Thus, the individual electronic cassettes 32 may be repeatedly used.

Inside the housing 54, the radiation detector 60 and a radiation detection section 62 are arranged in this order from the side of an irradiation surface 56 of the housing 54, onto which the radiation X is irradiated. The radiation detector 60 is for imaging a radiographic image according to the radiation X that has passed through an examinee. The radiation detection section 62 detects the irradiated radiation.

A case 31 that accommodates electronic circuits, including a microcomputer, and a rechargeable and detachable battery 96A is disposed at one end of the interior of the housing 54. The radiation detector 60 and the electronic circuits are operated by electrical power supplied from the battery 96A accommodated in the case 31. In order to prevent the various circuits accommodated inside the case 31 from being damaged due to irradiation of the radiation X, it is desirable for lead plating or the like to be provided at the irradiation surface 56 side of the case 31. The electronic cassette 32 relating to the present exemplary embodiment has a cuboid shape formed to be rectangular, and the case 31 is disposed at a portion at one end of the direction of the longest sides thereof.

A display unit 56A is provided at a predetermined location of an exterior wall of the housing 54. The display unit 56A implements displays representing operational states of the electronic cassette 32, including operation modes such as "Ready" and "Receiving data", a remaining amount state of the battery 96A and the like. In the electronic cassette 32 relating to the present exemplary embodiment, light emitting diodes are used as the display unit 56A, but this is not a limitation. Other display components may be used, such as light emitting elements other than light emitting diodes, a liquid crystal display, an organic electroluminescent display, or the like.

FIG. 4 shows a sectional diagram schematically illustrating structure of the radiation detector 60 and the radiation detection section 62 relating to the present exemplary embodiment.

The radiation detector 60 is provided with a TFT active matrix substrate (hereinafter referred to as a TFT substrate) 66 in which thin film transistors (hereinafter referred to as TFTs) 70 and storage capacitors 68 are formed on an insulating substrate 64.

A scintillator 71 that converts inputted radiation to light is disposed on the TFT substrate 66.

As the scintillator 71, for example, CsI:Tl or GOS may be used. However, the scintillator 71 is not limited to these materials.

It is sufficient that the insulating substrate 64 features transparency and has a small absorption with respect to the radiation. For example, a glass substrate, a transmissive ceramic substrate or a transparent resin substrate may be used. However, the insulating substrate 64 is not limited to these materials.

Sensor portions 72 that generate charges when the light converted by the scintillator 71 is incident thereon are formed in the TFT substrate 66. A flattening layer 67 for flattening the TFT substrate 66 is also formed in the TFT substrate 66. Between the TFT substrate 66 and the scintillator 71, an adhesion layer 69 for adhering the scintillator 71 to the TFT substrate 66 is formed on the flattening layer 67.

Each sensor portion 72 includes an upper electrode 72A, a lower electrode 72B, and a photoelectric conversion film 72C disposed between the upper and lower electrodes.

The photoelectric conversion film 72C absorbs light emitted from the scintillator 71, and generates electric charge in accordance with the absorbed light. The photoelectric conversion film 72C may be formed of a material that generates charge when irradiated with light, and may be formed of, for example, amorphous silicon, an organic photoelectric conversion material or the like. If the photoelectric conversion film 72C includes amorphous silicon, then it has a broad absorption spectrum and may absorb light emitted by the scintillator 71. If the photoelectric conversion film 72C includes an organic photoelectric conversion material, then it has a sharp absorption spectrum in the visible range and hardly any electromagnetic waves apart from the light emitted from the scintillator 71 are absorbed by the photoelectric conversion film 72C. Thus, noise that is caused by the absorption of radiation such as X-rays and the like at the photoelectric conversion films 72C may be effectively suppressed.

The present exemplary embodiment has a configuration in which an organic photoelectric conversion material is included in the photoelectric conversion films 72C. Examples of the organic photoelectric conversion material include, for example, quinacridone-based organic compounds and phthalocyanine-based organic compounds. As an example, quinacridone has an absorption peak wavelength of 560 nm, in the visible range. Therefore, if quinacridone is used as the organic photoelectric conversion material, and CsI(Tl) is used as the material of the scintillator 71, a difference between the absorption peaks may be kept to within 5 nm, and charge amounts generated by the photoelectric conversion films 72C may be substantially maximized. Organic photoelectric conversion materials that may be employed as the photoelectric conversion films 72C are described in detail in JP-A No. 2009-32854, so are not described here.

FIG. 5 schematically illustrates structure of each TFT 70 and storage capacitor 68 of the TFT substrate 66 relating to the exemplary embodiment.

The storage capacitor 68 and the TFT 70 are formed on the insulating substrate 64, in correspondence with the respective lower electrode 72B. The storage capacitor 68 stores charge that migrates from the lower electrode 72B. The TFT 70 converts the charge stored in the storage capacitor 68 to an electronic signal, and outputs the electronic signal. The region in which the storage capacitor 68 and TFT 70 are formed includes a region that is superposed with the lower electrode 72B in plan view. Thus, with this configuration, the storage capacitor 68 and the TFT 70 of each pixel are overlaid with the sensor portion 72 in the thickness direction, and the storage capacitor 68 and TFT 70 and the sensor portion 72 may be disposed in small areas.

An insulation film 65A is provided between the insulating substrate 64 and the lower electrodes 72B. Each storage capacitor 68 is electrically connected to the corresponding lower electrode 72B via wiring of a conductive material that is formed to penetrate through the insulation film 65A. Thus, charge collected in the lower electrode 72B may be allowed to migrate to the storage capacitor 68.

In each TFT 70, a gate electrode 70A, a gate insulation film 65B and an active layer (a channel layer) 70B are layered. A source electrode 70C and a drain electrode 70D are formed, with a predetermined gap formed therebetween, on the active layer 70B. In the radiation detector 60, the active layers 70B are formed of a non-crystalline oxide. The non-crystalline oxide constituting the active layers 70B is preferably an oxide including at least one of indium, gallium and zinc (for example, In—O), is more preferably an oxide including at least two of indium, gallium and zinc (for example, In—Zn—O, In—Ga—O or Ga—Zn—O), and is particularly preferably an oxide including indium, gallium and zinc. An In—Ga—Zn—O non-crystalline oxide is preferably a non-crystalline oxide whose composition in a crystalline state is represented by $InGaO_3(ZnO)_m$ (m being a natural number of less than 6), and is particularly preferably $InGaZnO_4$.

If the active layers 70B of the TFTs 70 are formed of a non-crystalline oxide, it does not absorb radiation such as X-rays or the like, or even if it does absorb such radiation, the radiation is only retained in tiny amounts. Therefore, the production of noise may be effectively suppressed.

The non-crystalline oxide that constitutes the active layers 70B of the TFTs 70, the organic photoelectric conversion material that constitutes the photoelectric conversion films 72C, and suchlike are all capable of film formation at low temperature. Therefore, the insulating substrate 64 is not limited to being a substrate with a high heat resistance, such as a semiconductor substrate, a quartz substrate, a glass substrate or the like; a flexible substrate of plastic or the like, or a substrate using aramid or bionanofibers may be used. Specifically, a flexible substrate of a polyester such as polyethylene terephthalate, polybutylene phthalate, polyethylene naphthalate or the like, or a polystyrene, polycarbonate, polyether sulfone, polyarylate, polyimide, polycycloolefin, polynorbornene resin, poly(chlorotrifluoro ethylene) or the like may be used. If a flexible substrate made of such a plastic is used, a reduction in weight may be promoted, which is useful for, for example, portability and the like. On the insulating substrate 64, the following layers may be provided: an insulating layer for ensuring insulation; a gas barrier layer for preventing permeation of moisture, oxygen and the like; an undercoating layer for improving flatness and contact with the electrodes and the like; and so forth.

With aramid, a heating process up to over 200° C. may be applied. Therefore, a transparent electrode material may be cured at high temperature and resistance may be lowered. Moreover, automatic mounting to a driver chip including a solder reflow step may be applied. Aramid has a thermal expansion coefficient close to that of ITO (indium tin oxide) or a glass substrate or the like. Therefore, there is little curling after fabrication and breakage is unlikely. Aramid may form a thinner substrate than a glass substrate or the like. An ultra-thin glass substrate and aramid may be laminated to form the insulating substrate 64.

A bionanofiber is a combination of cellulose microfibril bundles (microbial cellulose) produced by bacteria (Acetobacter Xylinum) and a transparent resin. The cellulose microfibril bundles have widths of 50 nm and a size 1/10 of a visible light wavelength, and have high strength, high resilience and low thermal expansion. The microbial cellulose is immersed in a transparent resin such as an acrylic resin, epoxy resin or the like, and the resin is hardened. Thus, bionanofibers are provided that contain 60-70% fibers and exhibit a transparency of about 90% for a wavelength of 500 nm. The bionanofibers have a low thermal expansion coefficient (3-7 ppm) compared with silicon crystal, have a strength comparable with steel (460 MPa) and a high resilience (30 GPa), and are flexible. Therefore, a thinner insulating substrate 64 may be formed than from a glass substrate or the like.

Figure 6:
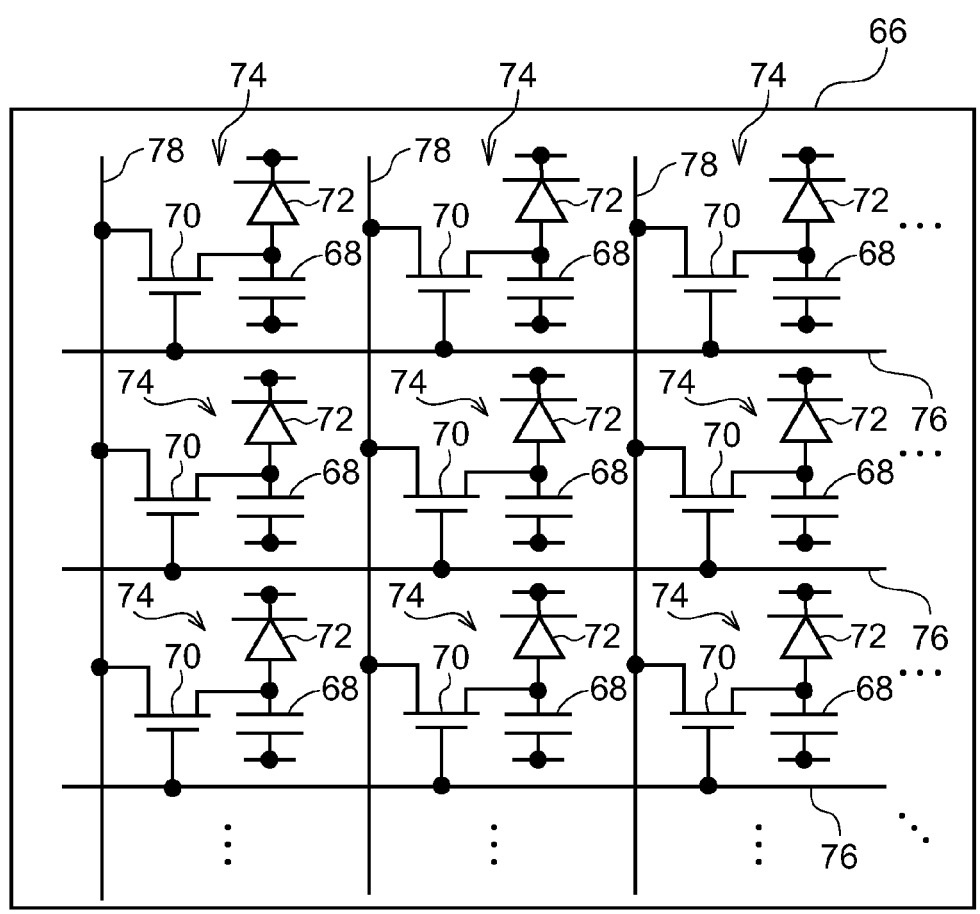
FIG. 6 is a plan diagram illustrating structure of a TFT substrate relating to the exemplary embodiment.

FIG. 6 shows a plan diagram illustrating structure of the TFT substrate 66 relating to the exemplary embodiment.

In the TFT substrate 66, pixels 74 that are each structured to include the aforementioned sensor portion 72, storage capacitor 68 and TFT 70 are plurally provided in a two-dimensional arrangement in a certain direction (the column direction in FIG. 6) and a direction crossing the certain direction (the row direction in FIG. 6). For example, if the radiation detection section 62 has a size of 17 inches by 17 inches, the pixels 74 are arranged in 2,880 rows and 2,880 columns.

Plural gate lines 76 and plural data lines 78 are provided in the TFT active matrix substrate 66. The gate lines 76 extend in the certain direction (the column direction) and are for turning the TFTs 70 of the pixel portions 74 on and off. The data lines 78 extend in the direction crossing the gate lines 76 (the row direction) and are for reading out the accumulated charges via the TFTs 70 that have been turned on.

The radiation detector 60 has a flat-plate form, in a quadrilateral shape with four outer edges in plan view. Specifically, the radiation detector 60 is formed in a rectangular shape.

As illustrated in FIG. 4, the radiation detector 60 relating to the present exemplary embodiment is formed by the scintillator 71 being adheringly attached to a surface of the TFT substrate 66.

If the scintillator 71 is formed of, for example, rod crystals such as CsI:Tl or the like, the scintillator 71 is formed by vapor deposition onto a vapor deposition substrate 73. When the scintillator 71 is formed by this vapor deposition, the vapor deposition substrate 73 may employ a plate of aluminium with a view to transmissivity of X-rays and cost, and must have a certain amount of thickness (of the order of several millimetres) for handling during vapor deposition, avoiding warping due to its own weight, deformation due to radiant heat, and the like.

The radiation detection section 62 is adheringly attached to the face of the radiation detector 60 at the side thereof at which the scintillator 71 is disposed.

In the radiation detection section 62, as an example, a wiring layer 142 in which wires 160 (FIG. 8) are patterned, which is described below, and an insulation layer 144 are formed on a support substrate 140 made of resin. Plural sensor portions 146 are formed thereon, and a scintillator 148 formed of GOS or the like is formed over the sensor portions 146. Each sensor portion 146 includes an upper electrode 147A, a lower electrode 147B, and a photoelectric conversion film 147C disposed between the upper and lower electrodes. The photoelectric conversion film 147C generates electric charge in response to the incidence of light converted by the scintillator 148. This photoelectric conversion film 147C is preferably a photoelectric conversion film containing the above-described organic photoelectric conversion material, rather than a PIN-type or MIS-type photodiode that uses amorphous silicon. The reason for this is that using a photoelectric conversion film containing an organic photoelectric conversion material is more advantageous in regard to reducing fabrication costs and acquiring flexibility than if a PIN photodiode or an MIS photodiode is used. There is no need for the sensor portions 146 of the radiation detection section 62 to be formed as finely as the sensor portions 72 provided in the pixels 74 of the radiation detector 60; the sensor portions 146 may be larger than the sensor portions 72, and may be formed with a size corresponding to tens or hundreds of the pixels of the radiation detector 60.

Figure 7:
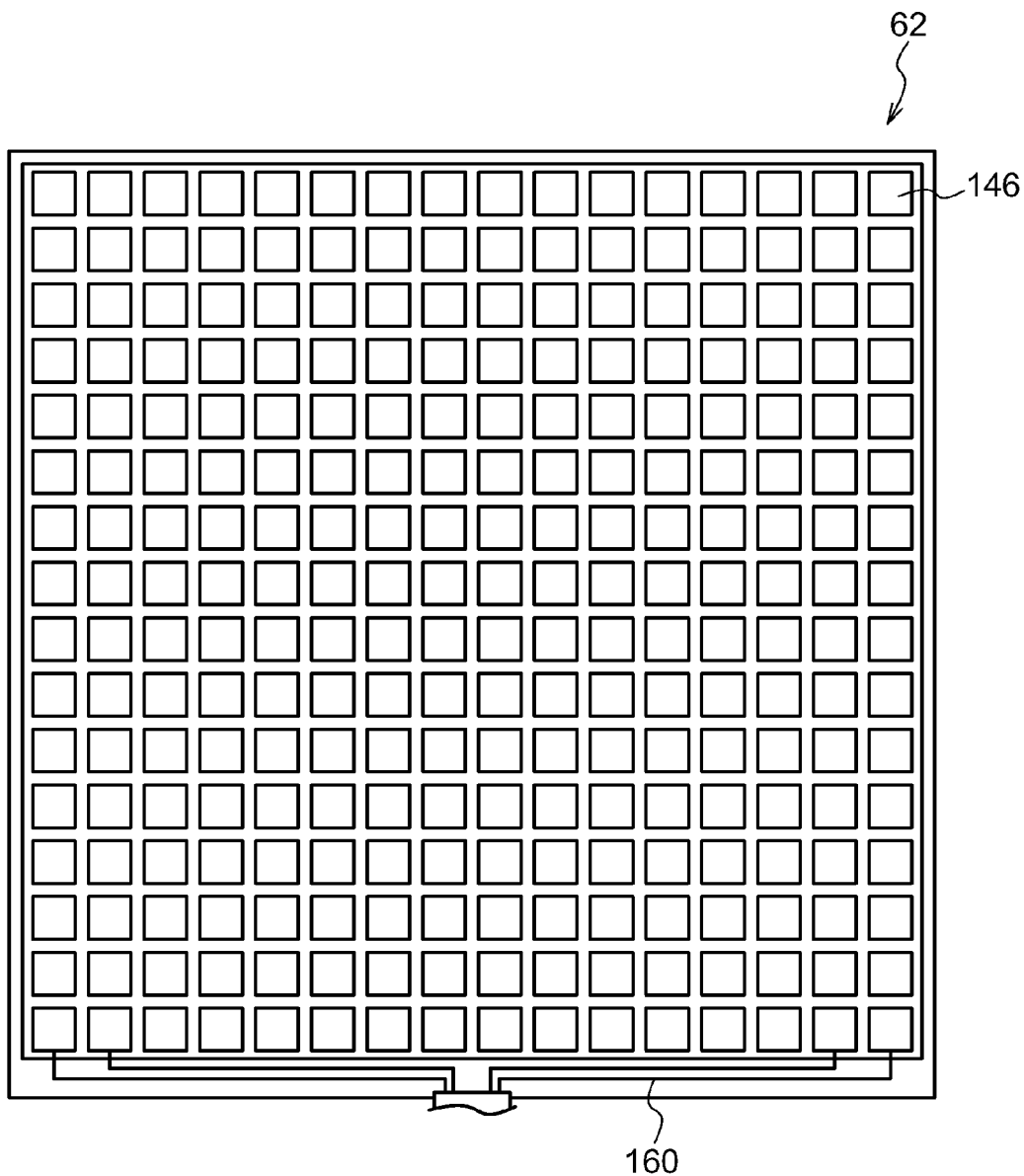
FIG. 7 is a plan diagram illustrating a wiring configuration of sensor portions of the radiation detection section relating to the exemplary embodiment.

FIG. 7 shows a plan diagram illustrating a wiring configuration of the sensor portions 146 of the radiation detection section 62 relating to the present exemplary embodiment.

In the radiation detection section 62, the sensor portions 146 are plurally arrayed in a certain direction (the column direction of FIG. 7) and a direction crossing the certain direction (the row direction of FIG. 7). For example, the sensor portions 146 are arranged in a matrix of 16 rows and 16 columns.

Figure 8:
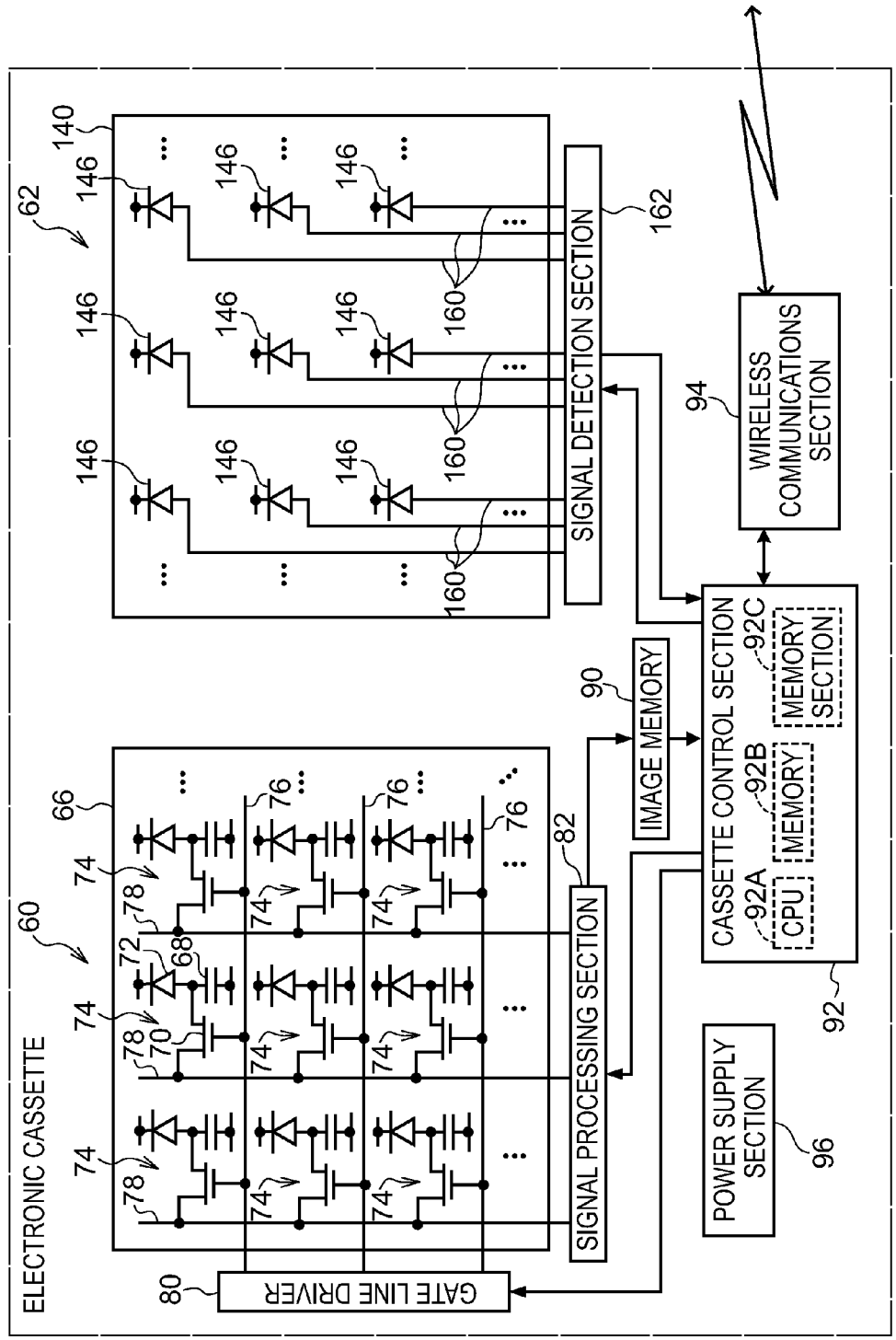
FIG. 8 is a block diagram illustrating principal structures of an electronic system of an electronic cassette relating to the exemplary embodiment.

FIG. 8 shows a block diagram illustrating principal structures of the electronic system of the electronic cassette 32 relating to the present exemplary embodiment.

As described above, in the radiation detector 60, the pixels 74 provided with the sensor portions 72, storage capacitors 68 and TFTs 70 are numerously arranged in a matrix. Charges that are generated by the sensor portions 72 in response to irradiation of the radiation X on the electronic cassette 32 are stored in the storage capacitors 68 of the individual pixels 74. Thus, image information carried by the radiation X irradiated at the electronic cassette 32 is converted to electric charges and retained in the radiation detector 60.

The respective gate lines 76 of the radiation detector 60 are connected to a gate line driver 80, and the respective data lines 78 are connected to a signal processing section 82. When charges are accumulated in the storage capacitors 68 of the respective pixels 74, the TFTs 70 of the respective pixels 74 are turned on sequentially, column by column, by signals provided through the gate lines 76 from the gate line driver 80. The charges accumulated in the storage capacitors 68 of the pixels 74 whose TFTs 70 have been turned on are transferred through the data lines 78 as analog electronic signals and inputted to the signal processing section 82. Thus, the charges accumulated in the storage capacitors 68 of the respective pixels 74 are sequentially read out column by column.

Figure 9:
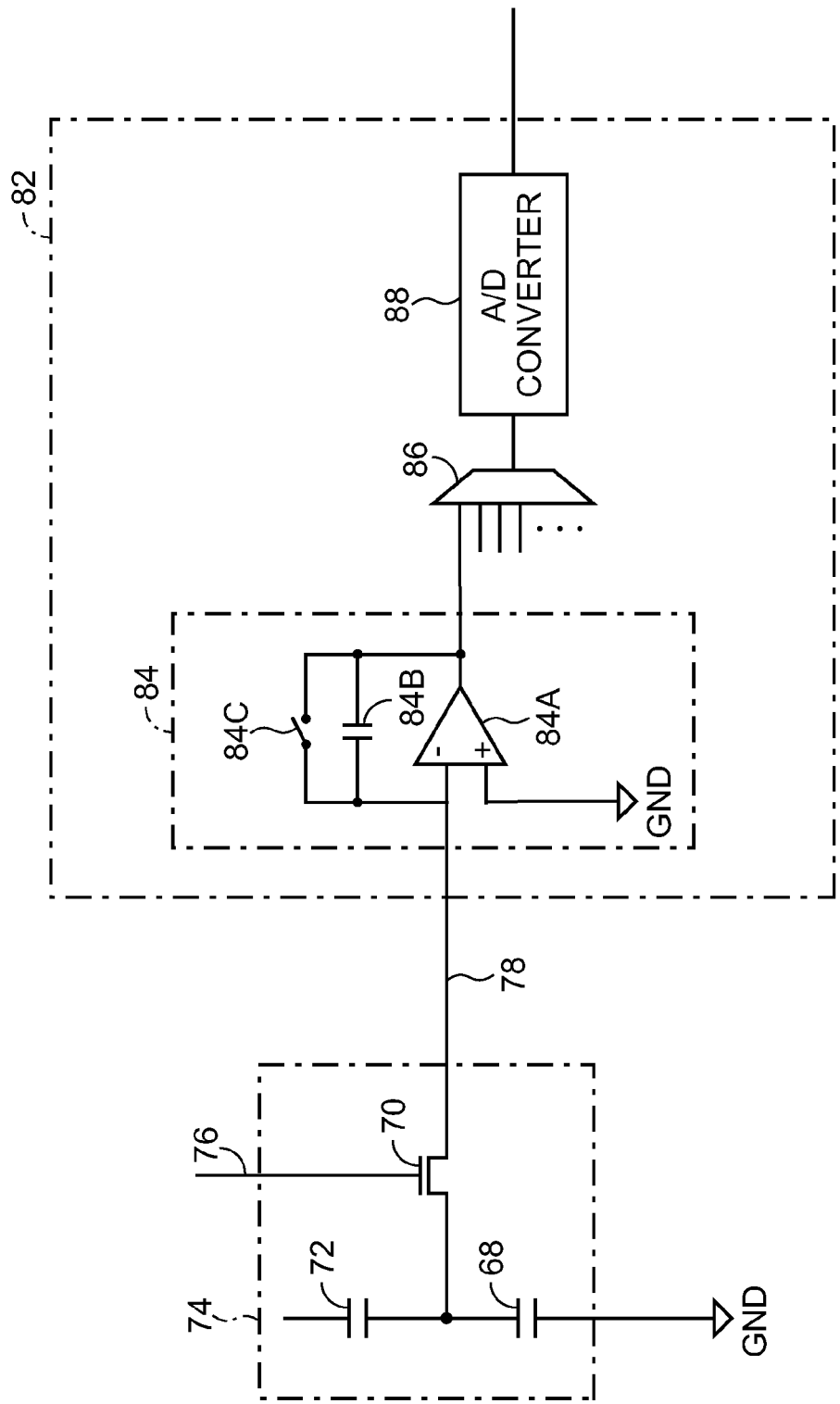
FIG. 9 is an equivalent circuit diagram concerning a single pixel portion of the radiation detector relating to the exemplary embodiment.

FIG. 9 is an equivalent circuit diagram concerning a single pixel portion of the radiation detector 60 relating to the present exemplary embodiment.

As illustrated in FIG. 9, the source of each TFT 70 is connected to the data line 78, and the data line 78 is connected to the signal processing section 82. The drain of the TFT 70 is connected to the storage capacitor 68 and the sensor portion 72, and the gate of the TFT 70 is connected to the gate line 76.

The signal processing section 82 is provided with an individual sample and hold circuit 84 for each data line 78. The electronic signals transferred through the respective data lines 78 are retained at the sample and hold circuits 84. Each sample and hold circuit 84 is constituted to include an op amp 84A and a capacitor 84B, and converts the electronic signals to analog voltages. The sample and hold circuit 84 is further provided with a switch 84C, which serves as a reset circuit that shorts together the two electrodes of the capacitor 84B and discharges charge accumulated in the capacitor 84B. The gain of the op amp 84A is adjustable by control from a cassette control section 92, which is described below.

A multiplexer 86 and an analog-to-digital (A/D) converter 88 are connected, in this order, to the output side of the sample and hold circuits 84. The electronic signals retained by the respective sample and hold circuits are converted to analog voltages, sequentially (serially) inputted into the multiplexer 86, and converted to digital image information by the A/D converter 88.

An image memory 90 is connected to the signal processing section 82 (see FIG. 8). The image information outputted from the A/D converter 88 of the signal processing section 82 is sequentially stored in the image memory 90. The image memory 90 has a storage capacity capable of storing a predetermined number of frames of image data. Each time a radiographic image is imaged, image data obtained by the imaging is sequentially stored in the image memory 90.

The image memory 90 is connected with a cassette control section 92 that controls overall operations of the electronic cassette 32. The cassette control section 92 is configured to include a microcomputer, and is provided with a central processing unit (CPU) 92A, a memory 92B including read-only memory (ROM) and random access memory (RAM), and a non-volatile memory section 92C constituted with a hard disc drive (HDD), flash memory or the like.

A wireless communications section 94 is connected to the cassette control section 92. The wireless communications section 94 relating to the present exemplary embodiment complies with wireless LAN (local area network) standards, as typified by IEEE (Institute of Electrical and Electronics Engineers) 802.11a/b/g and the like. The wireless communications section 94 controls transfers of various kinds of information between the cassette control section 92 and external equipment by wireless communications. The cassette control section 92 is capable of wireless communications with the console 42 via the wireless communications section 94, and may exchange various kinds of information with the console 42.

At the radiation detection section 62, as described above, the sensor portions 146 are numerously arranged in a matrix. The plural wires 160 are provided in the radiation detection section 62, and are respectively separately connected to the sensor portions 146. The wires 160 are connected to a signal detection section 162.

The signal detection section 162 is provided with a respective amplifier and A/D converter for each of the wires 160, and is connected to the cassette control section 92. In accordance with control by the cassette control section 92, the signal detection section 162 samples each wire 160 at predetermined intervals, converts electronic signals transmitted through the wires 160 to digital data, and sequentially outputs the converted digital data to the cassette control section 92.

A power supply section 96 is provided in the electronic cassette 32. The various circuits and components described above (the gate line driver 80, the signal processing section 82, the image memory 90, the wireless communications section 94, the cassette control section 92, the signal detection section 162 and so forth) are driven by electrical power supplied from the power supply section 96. The power supply section 96 incorporates the aforementioned battery (a rechargeable secondary cell) 96A so as not to impede portability of the electronic cassette 32, and provides power to the various circuits and elements from the charged battery 96A. The cassette control section 92 may acquire a remaining power amount (in Watt-hours) of the battery 96A. Wiring connecting the power supply section 96 with the various circuits and elements is not illustrated in FIG. 8.

Figure 10:
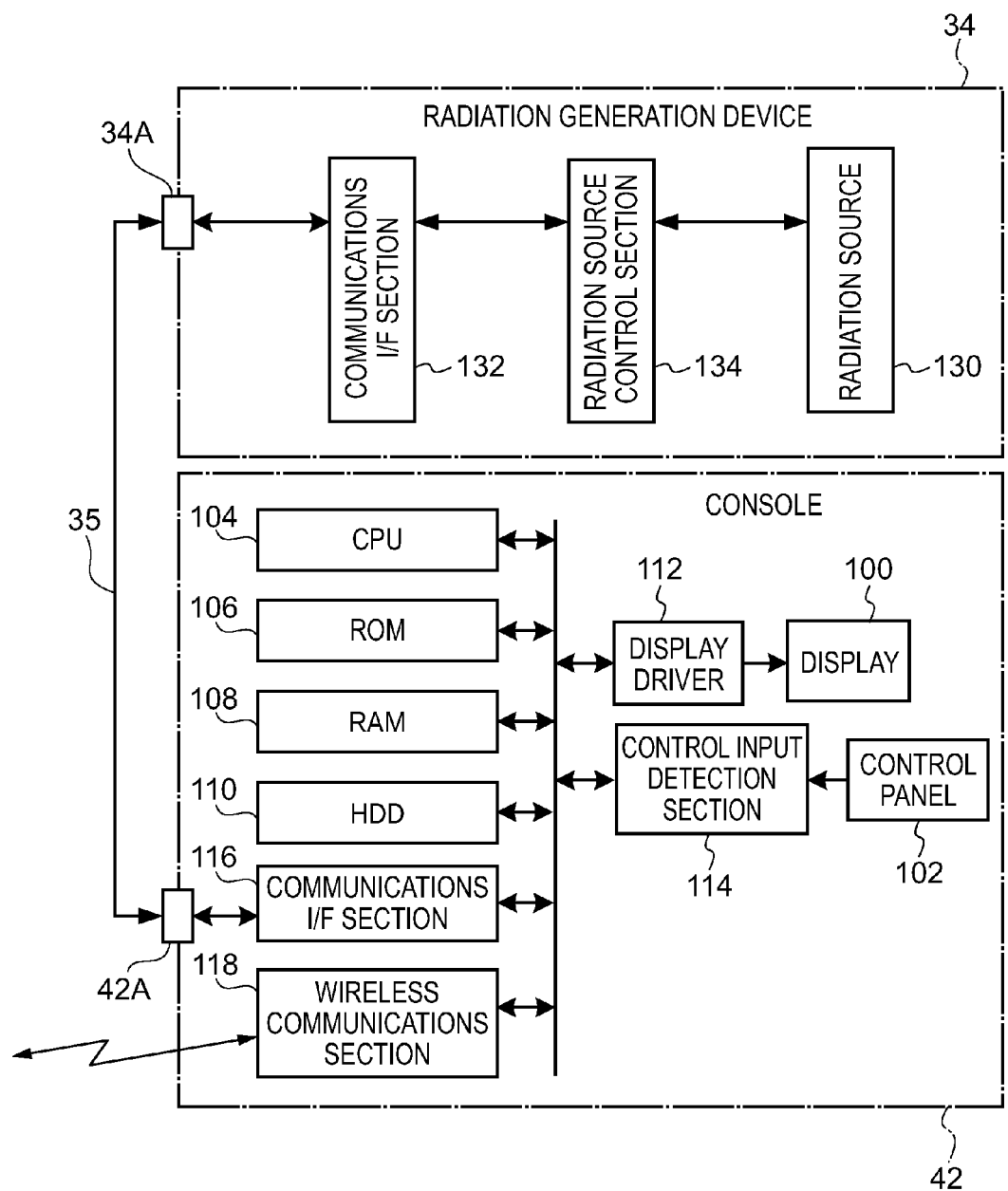
FIG. 10 is a block diagram illustrating principal structures of electronic systems of a console and a radiation generation device relating to the exemplary embodiment.

FIG. 10 shows a block diagram illustrating principal structures of electronic systems of the console 42 and the radiation generation device 34 relating to the present exemplary embodiment.

The console 42 is configured as a server computer. The console 42 is provided with a display 100, which displays control menus, captured radiographic images and the like, and a control panel 102, which is configured to include plural keys and at which various kinds of information and control instructions are inputted.

The console 42 relating to the present exemplary embodiment is provided with: a CPU 104 that administers operations of the device as a whole; a ROM 106 at which various programs, including a control program, and suchlike are stored in advance; a RAM 108 that temporarily stores various kinds of data; the HDD 110, which stores and retains various kinds of data; a display driver 112 that controls displays of various kinds of information at the display 100; and a control input detection section 114 that detects control states of the control panel 102. The console 42 is also provided with: a communications interface (I/F) section 116 that exchanges various kinds of information, such as below-described exposure conditions and the like, with the radiation generation device 34 via a connection terminal 42A and a communications cable 35; and a wireless communications section 118 that exchanges various kinds of information, such as the remaining power amount of the battery 96A and the like, with the electronic cassette 32 by wireless communications.

The CPU 104, the ROM 106, the RAM 108, the HDD 110, the display driver 112, the control input detection section 114, the communications I/F section 116 and the wireless communications section 118 are connected to one another by a system bus. Thus, the CPU 104 may access the ROM 106, the RAM 108 and the HDD 110, and may control displays of various kinds of information at the display 100 via the display driver 112, control exchanges of various kinds of information with the radiation generation device 34 via the communications I/F section 116, and control exchanges of various kinds of information with the electronic cassette 32 via the wireless communications section 118. The CPU 104 may also acquire states of control by users from the control panel 102 via the control input detection section 114.

The radiation generation device 34 is provided with the radiation source 130, a communications I/F section 132, and a radiation source control section 134. The communications I/F section 132 exchanges various kinds of information, such as the exposure conditions and the like, with the console 42. The radiation source control section 134 controls the radiation source 130 on the basis of received exposure conditions.

The radiation source control section 134 is configured to include a microcomputer, and stores the received exposure conditions and the like. The exposure conditions received from the console 42 include information such as a tube voltage and a tube current. The radiation source control section 134 causes the radiation X to be irradiated from the radiation source 130 in accordance with the received exposure conditions.

Next, operation of the imaging system 18 relating to the present exemplary embodiment is described.

When imaging of (a) radiographic image(s) is instructed, the console 42 displays an imaging menu input screen for input of imaging conditions at the display 100, and inputs are performed by an operator. In the imaging menu input screen, a message prompting the input of imaging menu choices, as exposure conditions for the subsequent imaging of the radiographic images, and an input region for this information are displayed. The imaging menu includes, for example, the name of the examinee of whom radiographic images are to be imaged, an imaging location, a posture during the imaging (in the present exemplary embodiment, reclining or standing), exposure conditions of the radiation X during the imaging (in the present exemplary embodiment, a tube voltage and tube current when the radiation X is emitted and an exposure duration), an imaging mode, a number of images, and so forth. The inputted imaging menu information is registered in, for example, the HDD 110.

The operator starts imaging of the radiographic image(s) in accordance with the exposure conditions inputted at the imaging menu input screen.

For example, as illustrated in FIG. 2, when an affected part of an examinee who is lying down on the reclining rack 46 is to be imaged, the operator disposes the electronic cassette 32 at the retention portion 152 of the reclining rack 46.

The operator designates still image imaging or radioscopic imaging as an imaging mode, designates, at the control panel 102, the tube voltage, tube current and the like for when the radiation X is irradiated, instructs the execution of imaging, and performs the imaging. In order to suppress irradiation of the examinee during radioscopic imaging, the operator designates a lower irradiation amount of radiation per unit time than when imaging a still image (for example, around 1/10 of when imaging a still image).

The console 42 sends the designated tube voltage and tube current to the radiation generation device 34 as exposure conditions, and sends the designated imaging mode, tube voltage, tube current and a tolerance amount to the electronic cassette 32 as imaging conditions. When the radiation source control section 134 of the radiation generation device 34 receives the exposure conditions from the console 42, the radiation source control section 134 stores the received exposure conditions, and when the cassette control section 92 of the electronic cassette 32 receives the imaging conditions from the console 42, the cassette control section 92 stores the received imaging conditions in the non-volatile memory section 92C.

When the operator has completed preparation for imaging, the operator performs an imaging start operation, which instructs imaging, at the control panel 102 of the console 42.

When the imaging start operation is performed at the control panel 102, instruction information instructing the start of exposure is sent to the radiation generation device 34 and the electronic cassette 32.

The radiation generation device 34 starts the generation and emission of radiation with the tube voltage and tube current according to the exposure conditions sent from the console 42.

When the cassette control section 92 of the electronic cassette 32 receives the instruction information instructing the start of exposure, the cassette control section 92 controls imaging in accordance with the imaging mode that has been stored as an imaging condition in the non-volatile memory section 92C.

Figure 11:
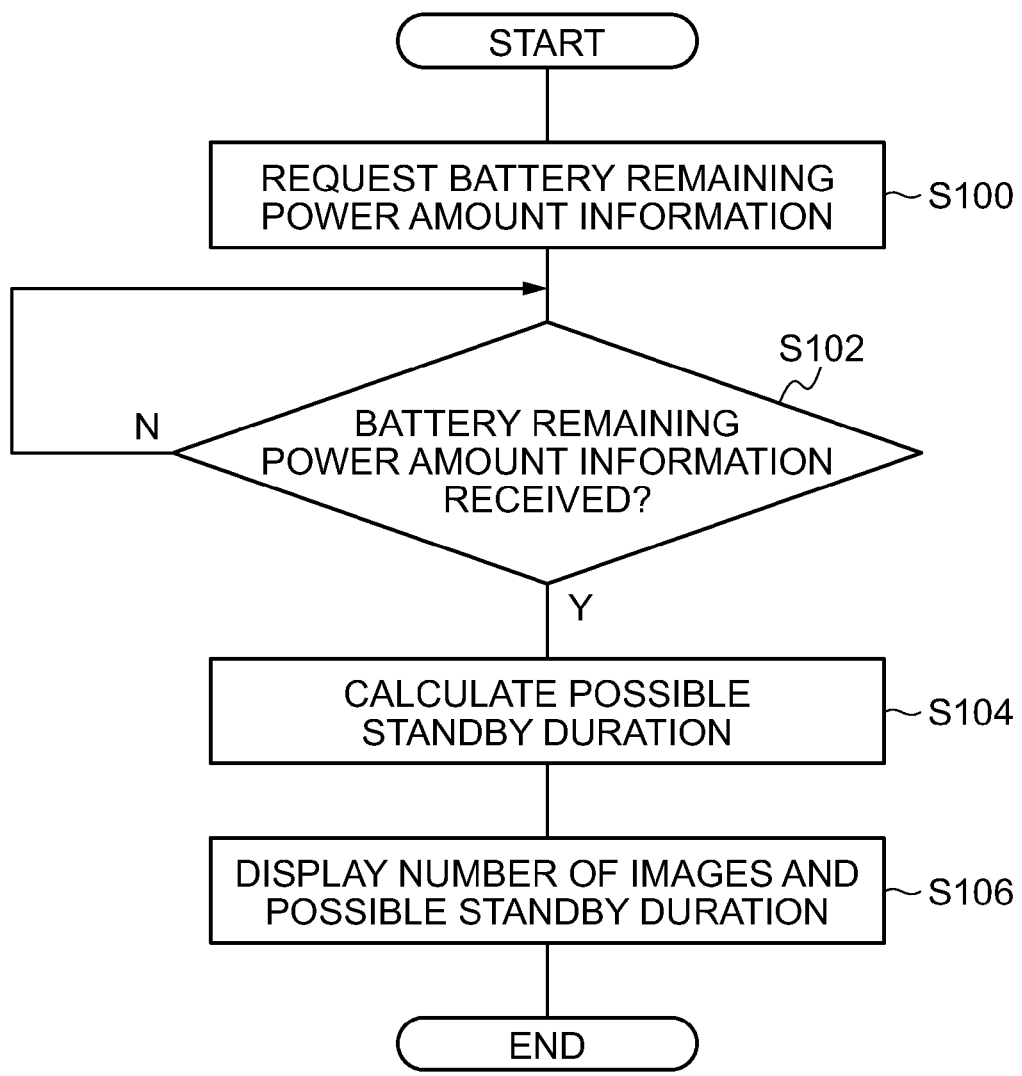
FIG. 11 is a flowchart illustrating a flow of processing of a control program relating to the exemplary embodiment.

FIG. 11 shows a flowchart illustrating a flow of processing of a control program that is executed by the CPU 104 of the console 42. This program is, for example, memorized in advance in a predetermined region of the HDD 110. The program is executed, for example, when imaging conditions are inputted at the imaging menu input screen.

First, in step S100, the electronic cassette 32 is requested to send battery remaining power amount information representing a remaining amount of battery power (in Wh) in the battery 96A of the electronic cassette 32. A signal representing this request is sent by the wireless communications section 118 and is received by the wireless communications section 94 of the electronic cassette 32.

Accordingly, the cassette control section 92 of the electronic cassette 32 senses the remaining power amount of the battery 96A, and sends battery remaining power amount information representing the sensed amount of power remaining in the battery to the console 42 via the wireless communications section 94.

In step S102, the CPU 104 determines whether or not the battery remaining power amount information has been received from the electronic cassette 32. While the battery remaining power amount information has not been received, the CPU 104 waits to receive the battery remaining power amount information, and when the battery remaining power amount information is received, the CPU 104 proceeds to step S104.

In step S104, the CPU 104 calculates a possible standby duration on the basis of the received battery remaining power amount information. This possible standby duration Twait (hours) is calculated by the following expression from the acquired battery remaining power amount Pbat (Wh), a number of images N of the patient to be imaged subsequently (a number), an imaging consumption power Pshot (Wh) that is consumed in imaging one shot, and a standby consumption power Pwait (Wh) that is consumed when in standby with no imaging being carried out.

$$T\text{wait} = (P\text{bat} - N \times P\text{shot})/P\text{wait} \quad (1)$$

That is, the possible standby duration is calculated on the basis of the remaining power, with imaging power that will be consumed by imaging being subtracted from the battery remaining power amount.

In the present exemplary embodiment, the number of images N is a number of images inputted (registered) at the imaging menu input screen, which is to say, a number of images required for examination of the individual patient who is to be imaged. Note that the number of images is not limited to a number of images inputted at the imaging menu input screen but may be, for example, a pre-specified maximum number of images for the hospital or radiography room in which the present device is disposed. That is, for example, in the case of a hospital or radiography room in which no more than N images are to be imaged for one patient, the number of images N is the maximum number of images for one patient.

The imaging consumption power Pshot that is consumed in imaging of one shot may be a pre-specified value for each set of imaging conditions, and may be an average value of power consumption when a plural number of images have been imaged under the same imaging conditions just before the calculation.

The standby consumption power Pwait may be a prespecified set value, and may be an average power consumption over a pre-specified standby period just before the calculation.

Now, when the voltage of the battery 96A drops, the imaging consumption power Pshot and the standby consumption power Pwait may increase due to a fall in efficiency of the power supply circuit of the power supply section 96. Accordingly, the possible standby duration of the electronic cassette 32 may be calculated by the following expression to take account of the output voltage of the battery 96A at such a time.

$$T\text{wait} = \{(P\text{bat} - N \times P\text{shot} \times k \times V\text{ful}/V\text{out})\}/(P\text{wait} \times k \times V\text{ful}/V\text{out}) \quad (2)$$

Here, k is a coefficient of a fall in efficiency with a fall in input voltage of the power supply circuit of the power supply section 96, Vful is the output voltage of the battery 96A when fully charged, and Vout is the output voltage of the battery 96A when the possible standby duration is calculated.

Thus, the possible standby duration may be calculated accurately by taking account of a fall in efficiency of the power supply circuit to calculate the possible standby duration.

In step S106, the possible standby duration calculated in step S104 and the number of images required for examination of the individual patient who will subsequently be imaged are displayed at the display 100. The possible standby duration and the number of images may be represented by numerical values, and may be represented graphically by a bar graph or the like.

If a number of images has not been registered at the imaging menu input screen, the pre-specified maximum number of images for the hospital or radiography room in which the present device is disposed may be displayed at the display 100 as the number of images N. If a number of images is subsequently registered at the imaging menu input screen, this registered number of images may be displayed at the display 100.

A display at the display 100 of a number of images registered at the imaging menu input screen and a display at the display 100 of the pre-specified maximum number of images for the hospital or radiography room in which the present device is disposed may be displayed with different colors.

Alternatively, if a number of images has not been registered at the imaging menu input screen, the number of images displayed at the display 100 may be set to zero, for the following reason. If a number of images were not registered at the imaging menu input screen and the maximum number were displayed at the display 100, the possible standby duration might be zero with the maximum number of images. Thus, even if there were actually spare capacity in the remaining power amount of the battery 96A and there was some possible standby duration, a misunderstanding that imaging was not possible might arise.

In the present exemplary embodiment, because the possible standby duration is displayed at the display 100, particularly for a patient of whom plural images are to be imaged, it may be easily understood how much of a margin there is for standby times between images. Therefore, the possibility of the remaining power amount in the battery 96A running short in the middle of an examination may be pre-emptively avoided.

The present invention has been described using an exemplary embodiment hereabove, but the technical scope of the present invention is not to be limited to the scope recited in the above exemplary embodiment. Various modifications and improvements may be applied to the above exemplary embodiment within a scope not departing from the spirit of the invention, and modes to which these modifications and improvements are applied fall within the technical scope of the present invention.

For example, in the present exemplary embodiment, a case has been described in which the possible standby duration and the number of images or the like are displayed at the display 100 of the console 42. However, a display may be provided at the electronic cassette 32 and displays implemented at this display.

Furthermore, the exemplary embodiment described above is not to limit the inventions relating to the claims, and means for achieving the invention are not necessarily to be limited to all of the combination of features described in the exemplary embodiment. Various stages of the invention are included in the above exemplary embodiment, and various inventions may be derived by suitable combinations of the plural structural elements that are disclosed. If some structural element is omitted from the totality of structural elements illustrated in the exemplary embodiment, as long as the effect thereof is provided, a configuration from which the some structural element is omitted may be derived to serve as the invention.

For example, in the above exemplary embodiment, a case is described in which the radiation detector 60 has an indirect conversion system in which radiation is temporarily converted to light, and the converted light is converted to electric charge at the sensor portions 72 and stored. However, the present invention is not to be limited thus. For example, the radiation detector 60 may have a direct conversion system that converts radiation to electric charge with a semiconductor layer of amorphous selenium or the like.

In the above exemplary embodiment, a case is described in which the present invention is applied to a radiographic imaging device that images radiographic images by detecting X-rays that serve as radiation, but the present invention is not to be limited thus. For example, the radiation that is the target of detection may be, beside X-rays, any of visible light, ultraviolet rays, infrared rays, gamma rays, particle rays and the like.

The configuration described in the above exemplary embodiment is an example. It will be clear to those skilled in the art that unnecessary portions may be removed, new portions may be added, and connection states and the like may be altered within a scope not departing from the spirit of the present invention.

Furthermore, the flow of processing of each kind of program described in the above exemplary embodiments (see FIG. 11) is an example. It will be clear to those skilled in the art that unnecessary steps may be removed, new steps may be added, and sequences of processing may be rearranged within a scope not departing from the spirit of the present invention.

What is claimed is:

1. A radiographic image imaging device comprising:
an acquisition component that acquires battery remaining power amount information representing an amount of power remaining in a battery, which is incorporated in a portable radiographic image imaging device and supplies power to the portable radiographic image imaging device, the portable radiographic image imaging device detecting radiation irradiated at a subject of imaging and generating a radiographic image;
a calculation component that calculates a possible standby duration of the portable radiographic image imaging device on the basis of the battery remaining power amount information acquired by the acquisition component and a number of images of the portable radiographic image imaging device; and
a display component that displays the number of images and the possible standby duration,
wherein the number of images is a number of images required for one patient, and
the calculation component subtracts an imaging power amount that is consumed by imaging of the number of images required for the one patient from the battery remaining power amount, and calculates the possible standby duration from a remaining power amount after the subtraction, wherein the number of images required for the one patient is a number of images for one patient that is specified in advance for a hospital in which the radiographic image imaging device is disposed.

2. The radiographic image imaging device of claim 1, wherein the calculation component calculates the possible standby duration of the portable radiographic image imaging device on the basis of the battery remaining power amount information acquired by the acquisition component, the number of images of the portable radiographic image imaging device, and an output voltage of the battery when fully charged and an output voltage of the battery when the possible standby duration is calculated.

3. The radiographic image imaging device of claim 1, wherein the number of images required for the one patient is a number of images designated in an imaging menu that is for designating imaging conditions.

4. The radiographic image imaging device of claim 3, wherein, if the designated number of images is designated in the imaging menu, the number of images required for the one patient is the designated number of images, and if a number of images is not designated in the imaging menu, the number of images required for the one patient is a maximum number of images for one patient that is specified in advance for a hospital in which the radiographic image imaging device is disposed.

5. The radiographic image imaging device of claim 4, wherein the display component changes a display color between a case in which a designated number of images is displayed and a case in which a maximum number of images for one patient is displayed.

6. The radiographic image imaging device of claim 1, wherein, if the number of images is designated in an imaging menu that is for designating imaging conditions, the display component displays the designated number of images, and if the number of images is not designated in the imaging menu, the display component displays the number of images as being zero.

7. A radiographic image imaging method comprising:

acquiring battery remaining power amount information representing an amount of power remaining in a battery, which is incorporated in a portable radiographic image imaging device and supplies power to the portable radiographic image imaging device, the portable radiographic image imaging device detecting radiation irradiated at a subject of imaging and generating a radiographic image;

calculating a possible standby duration of the portable radiographic image imaging device on the basis of the acquired battery remaining power amount information and a number of images of the portable radiographic image imaging device; and displaying the number of images and the possible standby duration;

wherein the number of images is a number of images required for one patient, and the calculation component subtracts an imaging power amount that is consumed by imaging of the number of images required for the one patient from the battery remaining power amount, and calculates the possible standby duration from a remaining power amount after the subtraction, and wherein the number of images required for the one patient is a number of images for one patient that is specified in advance for a hospital in which the radiographic image imaging device is disposed.

8. The radiographic image imaging method of claim 7, wherein the calculating includes calculating the possible standby duration of the portable radiographic image imaging device on the basis of the acquired battery remaining power amount information, the number of images of the portable radiographic image imaging device, and an output voltage of the battery when fully charged and an output voltage of the battery when the possible standby duration is calculated.

9. The radiographic image imaging method of claim 7, wherein the number of images is a number of images required for one patient, and the calculating includes subtracting an imaging power amount that is consumed by imaging of the number of images required for the one patient from the battery remaining power amount, and calculating the possible standby duration from a remaining power amount after the subtracting.

10. The radiographic image imaging method of claim 9, wherein the number of images required for the one patient is a maximum number of images for one patient that is specified in advance.

11. The radiographic image imaging method of claim 9, wherein the number of images required for the one patient is a number of images designated in an imaging menu that is for designating imaging conditions.

12. The radiographic image imaging method of claim 11, wherein, if the designated number of images is designated in the imaging menu, the number of images required for the one patient is the designated number of images, and if a number of images is not designated in the imaging menu, the number of images required for the one patient is a maximum number of images for one patient that is specified in advance.

13. The radiographic image imaging method of claim 12, wherein a display color differs between a case in which a designated number of images is displayed and a case in which a maximum number of images for one patient is displayed.

14. The radiographic image imaging method of claim 7, wherein the displaying includes, if the number of images is designated in an imaging menu that is for designating imaging conditions, displaying the designated number of images, and if the number of images is not designated in the imaging menu, displaying the number of images as being zero.

15. A non-transitory storage medium readable by a computer, the storage medium storing a program of instructions executable by the computer to function as a radiographic image imaging device that comprises:

an acquisition component that acquires battery remaining power amount information representing an amount of power remaining in a battery, which is incorporated in a portable radiographic image imaging device and supplies power to the portable radiographic image imaging device, the portable radiographic image imaging device detecting radiation irradiated at a subject of imaging and generating a radiographic image;

a calculation component that calculates a possible standby duration of the portable radiographic image imaging device on the basis of the battery remaining power amount information acquired by the acquisition component and a number of images of the portable radiographic image imaging device; and a display component that displays the number of images and the possible standby duration;

wherein the number of images is a number of images required for one patient, and the calculation component subtracts an imaging power amount that is consumed by imaging of the number of images required for the one patient from the battery remaining power amount, and calculates the possible standby duration from a remaining power amount after the subtraction, and wherein the number of images required for the one patient is a number of images for one patient that is specified in advance for a hospital in which the radiographic image imaging device is disposed.

16. The non-transitory storage medium of claim 15, wherein the calculation component calculates the possible standby duration of the portable radiographic image imaging device on the basis of the battery remaining power amount information acquired by the acquisition component, the number of images of the portable radiographic image imaging device, and an output voltage of the battery when fully charged and an output voltage of the battery when the possible standby duration is calculated.

17. The non-transitory storage medium of claim 15, wherein the number of images is a number of images required for one patient, and the calculation component subtracts an imaging power amount that is consumed by imaging of the number of images required for the one patient from the battery remaining power amount, and calculates the possible standby duration from a remaining power amount after the subtraction.

18. The non-transitory storage medium of claim 17, wherein the number of images required for the one patient is a maximum number of images for one patient that is specified in advance for a hospital in which the radiographic image imaging device is disposed.

* * * * *